United States Patent
Welik

(10) Patent No.: US 6,494,201 B1
(45) Date of Patent: Dec. 17, 2002

(54) PORTABLE OXYGEN DISPENSER

(76) Inventor: Ralph Welik, 5500 Avenue MacDonald, Suite 1605, Montreal, Quebec (CA), H3X 2W5

( * ) Notice: Subject to any disclaimer, the term of this patent is extended or adjusted under 35 U.S.C. 154(b) by 0 days.

(21) Appl. No.: 09/568,922

(22) Filed: May 11, 2000

(51) Int. Cl.$^7$ .............................................. A61M 11/00
(52) U.S. Cl. ........................... 128/200.23; 128/200.24; 128/204.18
(58) Field of Search ........................ 128/200.14–200.24, 128/203.12, 204.18; 222/3, 549, 559, 566; 251/155, 153, 213, 322, 323, 330, 349

(56) References Cited

U.S. PATENT DOCUMENTS

| | | | | |
|---|---|---|---|---|
| 3,012,555 A | * | 12/1961 | Meshberg | 128/200.23 |
| 3,209,751 A | * | 10/1965 | Wakeman | 128/200.23 |
| 4,582,054 A | * | 4/1986 | Ferrer | 128/200.23 |
| 5,571,246 A | * | 11/1996 | Alldredge | 128/200.23 |
| 5,724,962 A | * | 3/1998 | Vidgren et al. | 128/200.23 |

* cited by examiner

*Primary Examiner*—Glenn K. Dawson
(74) *Attorney, Agent, or Firm*—Ostrolenk, Faber, Gerb & Soffen, LLP

(57) ABSTRACT

A portable oxygen dispenser for providing an emergency supply of oxygen-rich gas includes a closed cannister defining a cannister axis and diameter and containing a quantity of pressurized, oxygen-rich. A dispensing orifice includes an externally actuable valve at one axial end of said cannister for maintaining the orifice normally closed. The valve includes a nozzle stem generally arranged along the cannister axis. An annular neck wall is generally concentrically arranged about the nozzle stem and dimensioned to form an annular space between the nozzle stem and the neck wall. A generally conical diffusing member defines a diffusion axis and opposing axial ends, one of which is a dispensing open end dimensioned to substantially correspond to the cannister diameter; the other end is a closed infusion end and is provided with an inlet opening defining an axis generally transverse to the diffusion axis and structure for engaging the stem for selectively applying an axial force to the nozzle stem. The dispensing end is configured to fit over the cannister when not in use. The cannister and the diffusion axes are generally aligned and adapted to be placed over the mouth and/or nose of a user. A protective guide extends into the annular space slidingly engaging the annular neck wall for substantially limiting the forces applied to the nozzle stem to axial forces along the cannister axis. In this way, forces on the nozzle stem other than the axial forces along the cannister axis are avoided, thus preventing damage to the nozzle stem during use of the diffusing member.

7 Claims, 1 Drawing Sheet

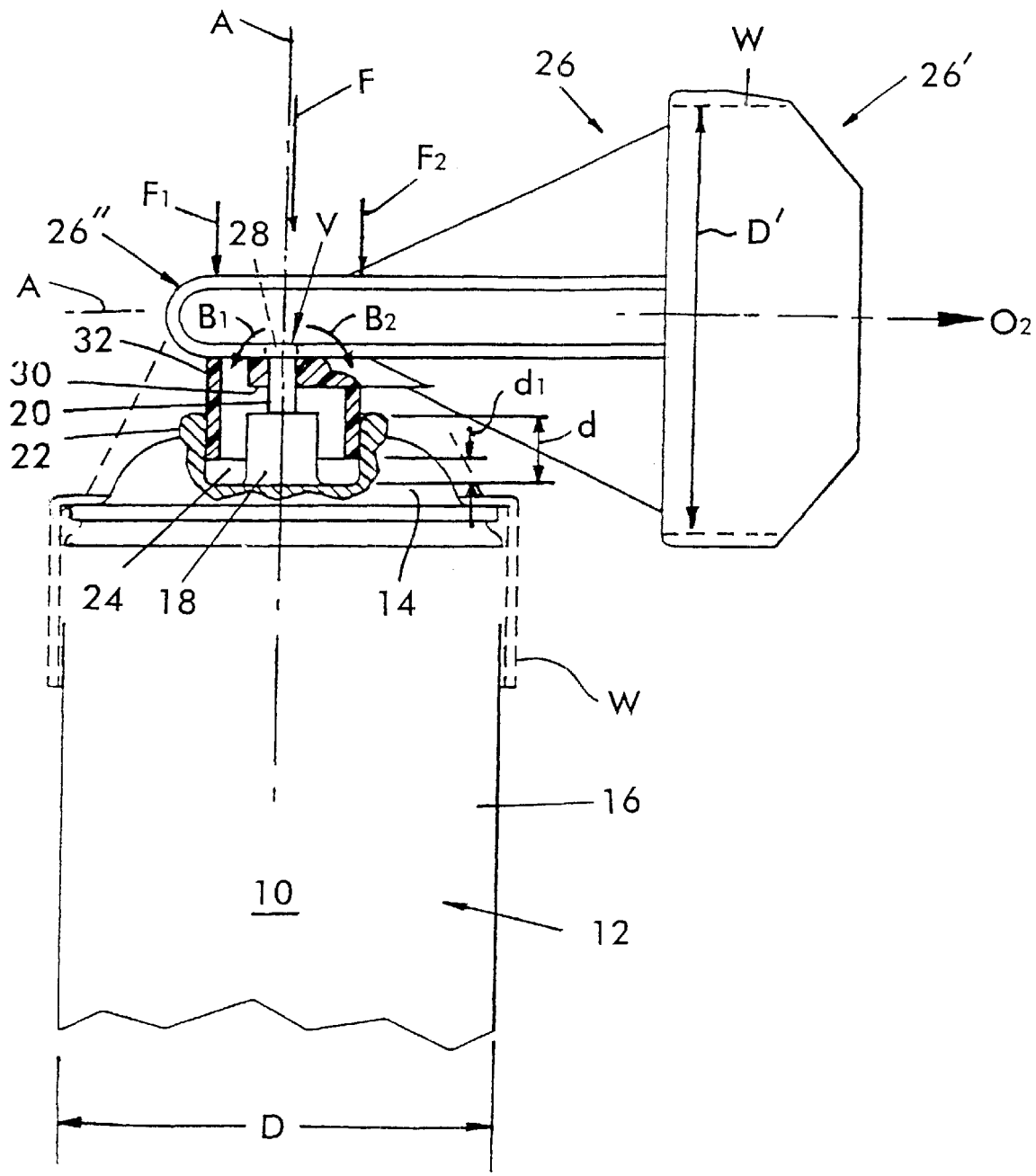

PORTABLE OXYGEN DISPENSER

BACKGROUND OF THE INVENTION

1. Field of the Invention

This invention generally relates to inhalers and, more particularly, to a portable oxygen dispenser.

2. Description of the Prior Art

Actuators for aerosol inhalers of various types have been proposed. In most instances, the devices are used for dispensing medicinal aerosol formulations. See, for example, U.S. Pat. No. 5,899,201. A dispensing package for material under pressure is also disclosed in U.S. Pat. No. 3,012,555. In these patents actuators are disclosed for specialized cannisters used for storing drugs for treating various disorders such as asthma, chronic bronchitis, emphysema and chronic obstructive pulmonary disease. The specialized cannisters are relatively small, and the actuators are designed to actuate the nozzle valve while engaging the outside rim or periphery of the cannister. In such cases, the actuator typically has a cylindrical housing portion the inner surface of which engages the outside rim or periphery of the cannister. This is also shown, for example, in U.S. Pat. Nos. 5,860,416 and 3,012,555. In most of these applications, the cannisters include a relatively small mouthpiece through which a patient can inhale a metered dose of a drug expelled from the aerosol cannister. Accordingly, both the actuators and the aerosol cannisters tend to be relatively small, and especially designed to cooperate with each other.

One of the difficulties with aerosol cannisters generally is that they typically include a nozzle or valve stem which is frequently in the form of a thin-walled small diameter tube made of a deformable material, such as plastic. Such stems are substantially stronger in compression, when axial forces are applied to them, than in bending when transverse forces are applied to them which causes such stems to bend and frequently break. Unfortunately, once the valve stem breaks, there is no other mechanism for opening the aerosol cannister valve and, therefore, the entire cannister and its contents must be discarded.

The same is normally true of more traditional aerosol cannisters or containers of the type, for example, frequently used for deodorants, hairsprays, cleaners, etc. In connection with more traditional consumer-oriented, off-the-shelf cannisters, very little is done to protect the valve or nozzle stems against bending and premature breakage. Such stems are designed with the intent of having the consumer apply a force to the valve stem that is generally aligned or coextensive with the axis of such stem. Under such conditions, the valve stem causes the valve to be opened and the contents to be released without jeopardizing the integrity of the stem. However, application of forces to the valve stem other than axial forces can cause bending and damage to such stem, as suggested.

SUMMARY OF THE INVENTION

Accordingly, it is an object of the invention to provide a portable oxygen dispenser which does not have the disadvantages associated with prior art aerosol cannisters.

It is another object of the invention to provide a portable oxygen dispenser which utilizes a conical diffusing member, particularly suitable for dispensing oxygen or a mixture of gases including oxygen.

It is still another object of the invention to provide a portable oxygen dispenser which uses a conventional aerosol cannister.

It is yet another object of the invention to provide a portable oxygen dispenser which includes a protective guide on the conical diffusing member which eliminates or minimizes the risk of damage or breakage of the nozzle-stem of the aerosol valve during use.

It is a further object of the invention to provide a portable oxygen dispenser which is easier to use under various conditions without risk of damage to the valve stem which releases the oxygen or oxygen mixture.

It is still a further object of the invention to provide a portable oxygen dispenser which is simple in construction and economical to manufacturer.

It is yet a further object of the present invention to provide a portable oxygen dispenser which has a dual purpose diffuser member that can be used, on the one hand, to receive the oxygen from a cannister and diffuse it for intake by a user through the nose and/or mouth, and, on the other hand, to cover that end of the cannister which includes the cannister valve and nozzle stem and protects the same when not in use.

In order to achieve the above objects, as well as others which will become evident hereinafter, a portable oxygen dispenser in accordance with the present invention for providing an emergency supply of oxygen-rich gas comprises a closed cannister having a top closure portion in a cylindrical side wall defining a cannister axis in diameter and containing a quantity of oxygen-rich gas in a pressurized condition. A dispensing orifice includes an externally actuatable valve means at one axial end of said cannister for maintaining said dispensing orifice in a normally closed condition. Said valve means includes a nozzle stem generally arranged along said cannister axis for opening said orifice when an axial force is applied thereto. An annular neck wall is generally concentrically arranged about said nozzle stem and dimensioned to form an annular space between the nozzle stem and said neck wall. A generally conical diffusing member defines a diffusion axis and opposing axial ends, one of which is a dispensing open end dimensioned to substantially correspond to said cannister diameter, and the other end of which is a closed infusion end provided with an inlet opening defining an axis generally transverse to said diffusion axis and stem engaging means for selectively applying an axial force to said nozzle stem. Said one dispensing end is configured to fit over and be supported on said cannister when not in use, and said cannister and said diffusion axes are generally aligned and are adapted to be placed over the mouth and/or nose of a user. Protective guide means is provided extending from said closed infusion end along said transverse axis into said annular for slidingly engaging said annular neck wall with little clearance during use once said cannister and transverse axes are generally aligned and oxygen-rich gas is to be released and for substantially limiting forces applied to said nozzle stem to axial forces along said cannister axis. In this manner, forces on said nozzle stem other than said axial forces along said cannister axis are avoided, thereby to prevent damage to said nozzle stem during use of said diffusing member.

BRIEF DESCRIPTION OF THE DRAWING

Other aspects, objects and advantages of the present invention will become apparent upon reading of the following detailed description of the preferred embodiment of the present invention when taken in conjunction with the drawing, as follows.

The single FIGURE is a side elevational view of a portable oxygen dispenser in accordance with the present invention, partially broken away to illustrate the details of the nozzle stem of the cannister valve and the manner in which it is protected against bending forces when the conical diffusing member is arranged as shown during normal use.

DESCRIPTION OF PREFERRED EMBODIMENT

Referring now to the FIGURE, a portable oxygen dispenser in accordance with the present invention for providing an emergency supply of oxygen-rich gas is generally designated by the reference numeral 10.

The dispenser 10 includes a closed aerosol container or cannister 12. The cannister 12 is generally a right cylindrical cannister having a circular cross section defining a cannister axis A. The cannister 12 has a top closure portion in the form of a top wall 14 and a cylindrical side wall 16 defining a cannister diameter D and contains a quantity of oxygen-rich gas in a pressurized condition.

A conventional dispensing orifice 18 is formed in the top wall 14 which includes an externally actuatable valve V at one axial end of the cannister, as shown in the FIGURE, for maintaining the dispensing orifice in a normally closed condition. Such dispensing orifice or valve is well known and is used with conventional aerosol cannisters or containers for dispensing various substances, typically liquids including hairsprays, cleaners, deodorants, etc. As is typical with such aerosol valves, the valve includes a elongate nozzle stem 20 generally arranged along the cannister axis A. Normally, such nozzle stem 20 extends upwardly, as viewed in the FIGURE, to a normal or "rest" position when the valve is closed. Opening of the valve involves the application of an axial force represented by the arrow F in the FIGURE, which tends to provide an axial inward force on the nozzle stem 20. When the valve or nozzle stem 20 is depressed a predetermined amount Δ, it causes the valve to open and allows the pressurized contents to be released.

As is common with such aerosol containers or cannisters, there is provided an annular neck wall 22 which is generally concentrically arranged about the nozzle stem 20 and dimensioned to form an annular space 24 between the nozzle stem 20 and the neck wall 22. The annular space 24 is shown to have an axial height of "d".

In order to controllably receive and diffuse metered quantities of oxygen-rich gas, a generally conical diffusing member 26 is provided which defines a diffusion axis A' and opposing axial ends 26' and 26". Axial end 26' is a dispensing open end which is dimensioned to substantially conform to the size and shape of the exterior shape of the cannister. Therefore, the dispensing open end 26' is shown to have a diameter D' defined by a wall W of the member 26. The inside surface of the wall W is selected to substantially correspond to the diameter D so that when the device is not in use, the axial end 26' of the diffusing member 26 can be slipped over the upper axial end of the cannister 12, as suggested by the dashed outline. The diameter D', therefore, needs to substantially correspond to the diameter D of the cannister, although it should be slightly larger so that the diffusing member 26 can be slipped over the container or cannister with little clearance to preferably provide a slight friction fit. Such fit retains the diffusing member 26 on the cannister when not in use while allowing the diffusing member to be readily removed when needed and placed on the cannister as shown in the FIGURE.

The other end 26" of the diffusing member 26 is a closed diffusion end provided with an inlet opening 28 which defines an axis generally normal to the diffusion axis A' and shown substantially coextensive with the cannister axis A in the FIGURE. A stem engaging member 30 is provided for selectively applying an axial force to the nozzle stem 20 when the inlet opening 28 is aligned with the nozzle stem, as shown.

The dispensing open end 26' is configured to fit over and be supported on the cannister 12 when not in use, as indicated by the phantom outline representation of the axial end 26'. The cannister and the fusion axes are generally aligned when the diffusing member 26 is not in use and mounted on the cannister, as shown. The axial end 26' is also adapted to be placed over the mouth and/or nose of the user.

In accordance with an important feature of the invention, a suitable protective guide member 32 is provided that extends from the closed infusion end 26" along the transverse axis into the annular space 24 for slidingly contacting the inner surface of the annular neck wall 22 with little clearance during use, as shown, when the cannister and the transverse axes are generally aligned and oxygen-rich gas is to be released. The guide 32 substantially limits the forces applied to the nozzle stem 20 to axial forces along the cannister axis A.

When the diffusing member 26 is mounted on the aerosol cannister during use, as shown in the FIGURE, the application of a force F along the cannister axis A generally does not present a problem or danger to the nozzle stem 20. However, because of the relatively large size of the diffusing member 26, a user can, particularly under certain circumstances, inadvertently apply a force further remote from the axial end 26', such as force $F_1$, which would result in a counterclockwise bending moment $B_1$, while the application of a force $F_2$ more proximate to the axial end 26' would create a clockwise bending moment that would have the tendency to bend the nozzle stem 20 in the direction generally indicated by the arrow $B_2$ as viewed in the FIGURE. Thus, because the valve stem 20 can be readily deformed, unless the user applies a force precisely along the cannister axis A, it is important to protect the valve stem against excessive bending resulting in breakage, which would render the aerosol container or cannister useless.

In accordance with one embodiment of the invention, the protective guide 32 is in the form of a continuous annular cylindrical wall for making contact with the annular neck continuously about the cannister axis A when the diffusing member is mounted on the cannister during use. However, it will be clear to those skilled in the art that the guide 32 may also be in the form of a plurality of axial elements arranged to contact the inside surface of the annular neck when the diffusing member is mounted on the cannister, as shown.

As indicated in the FIGURE, the annular space 24 defines a predetermined axial height "d" along the cannister axis A. The guide 32 consists of a wall extending along the cannister axis and preferably projecting into the space 24 when the diffusing member is in use a distance equal to at least one half of the predetermined axial height "d", when in contact with but prior to application of axial force on the nozzle stem. The guide wall 32 forms a clearance $d_1$ at the lower end thereof prior to application of an axial force to the nozzle stem 20. The nozzle stem requires a predetermined axial displacement Δ to activate the valve, the clearance $d_1$ being greater than the predetermined axial displacement Δ needed to activate the valve so that the guide wall 32 has sufficient clearance to move downwardly or inwardly the requisite amount.

The specific construction of the protective guide 32 is not critical as long as it achieves the function of securely and reliably allowing axial movements of the diffusing member 26 along the cannister axis A while preventing excessive bending moments $B_1$ and $B_2$. In the presently preferred embodiment, the guide wall 32 is integrally formed with the conical diffusing member 26 and, for example, both may be molded from a plastic material.

The invention has been shown and described by way of a presently preferred embodiment, and many variations and modifications may be made therein without departing from the spirit of the invention. The invention, therefore, is not to be limited to any specified form or embodiment, except insofar as such limitations are expressly set forth in the claims.

What I claim:

1. A portable oxygen dispenser for providing an emergency supply of oxygen-rich gas, comprising a closed cannister having a top closure portion and a side wall defining a cannister axis and containing a quantity of oxygen-rich gas in a pressurized condition; a dispensing orifice including an externally actuable valve structure at one axial end of said cannister for maintaining said dispensing orifice in a normally closed condition, said valve structure including a nozzle stem generally arranged along said cannister axis for opening said orifice when a force is applied thereto; a neck wall generally arranged about said nozzle stem and dimensioned to form a space between said nozzle stem and said neck wall; a generally conical diffusing member defining a diffusion axis and opposing axial ends one of which is a dispensing open end dimensioned to substantially correspond to said cannister and the other end of which is a closed infusion end provided with an inlet opening defining an axis generally transverse to said diffusion axis and stem engaging structure that selectively applies an axial force to said nozzle stem, said one dispensing end being configured to fit over and be supported on said cannister when not in use and constructed to be placed over the mouth and/or nose of a user; and a protective guide extending from said closed infusion end and slidingly engaging said neck wall with little clearance during use when said cannister and transverse axes are generally aligned and oxygen-rich gas is to be released and substantially limiting forces applied to said nozzle stem to axial forces along said cannister axis, whereby forces on said nozzle stem other than said axial forces along said cannister axis are avoided to thereby prevent damage to said nozzle stem during use of said diffusing member.

2. A portable oxygen dispenser as defined in claim 1, wherein said protective guide comprises a continuous annular cylindrical wall for making contact with said neck continuously about said cannister axis when said diffusing member is mounted on said cannister during use.

3. A portable oxygen dispenser as defined in claim 1, wherein said protective guide comprises a plurality of axial elements arranged to contact said annular neck when said diffusing member is mounted on said cannister during use.

4. A portable oxygen dispenser as defined in claim 1, wherein said space defines a predetermined axial height along said cannister axis, said protective guide comprising a wall extending along said cannister axis and projecting into said space when said diffusing member is in use, a distance equal to at least one half of said predetermined axial height when in contact with but prior to application of axial force in said nozzle stem.

5. A portable oxygen dispenser as defined in claim 4, wherein said wall of said protective guide means defines a clearance at the axial lower end thereof prior to application of an axial force to said nozzle stem, the nozzle stem requiring a predetermined axial displacement to activate the valve, said clearance having an axial height greater than said predetermined axial displacement.

6. A portable oxygen dispenser as defined in claim 1, wherein said protective guide is integrally formed with said conical diffusing member.

7. A portable oxygen dispenser as defined in claim 6, wherein said conical diffusing member is molded from a plastic material.

* * * * *